United States Patent [19]

Voegeli et al.

[11] Patent Number: 5,322,839
[45] Date of Patent: Jun. 21, 1994

[54] PROTEIN FRACTION FOR COSMETIC AND DERMATOLOGY CARE OF THE SKIN

[75] Inventors: Rainer Voegeli, Bubendorf; Kurt Stocker, Aesch; Christian Mueller, Reinach, all of Switzerland

[73] Assignee: Pentapharm AG

[21] Appl. No.: 943,848

[22] Filed: Sep. 11, 1992

[30] Foreign Application Priority Data

Sep. 13, 1991 [CH] Switzerland ............ 02705/91

[51] Int. Cl.$^5$ ............ A61K 37/02; A61K 37/64
[52] U.S. Cl. ............ 514/21; 530/378; 530/370; 530/300; 514/886; 514/947; 514/969
[58] Field of Search ............ 530/378, 300, 350, 370, 530/377; 514/886, 2, 873, 947, 969; 424/195.1

[56] References Cited

U.S. PATENT DOCUMENTS

| | | | |
|---|---|---|---|
| 2,794,800 | 6/1957 | Rienks et al. | 260/236.5 |
| 4,240,450 | 12/1980 | Grollier et al. | 424/61 |
| 4,696,813 | 9/1987 | Higa | 514/21 |

FOREIGN PATENT DOCUMENTS

0420600A2  4/1991  European Pat. Off. .
0420600    4/1991  European Pat. Off. .

OTHER PUBLICATIONS

Hwang, et al. Biochim. Biophys. Acta 495, 369-382 (1977).
Gatehouse, et al. Phytochemistry 19, 751-759 (1980).

*Primary Examiner*—Michael G. Wityshyn
*Assistant Examiner*—C. Sayala
*Attorney, Agent, or Firm*—Pennie & Edmonds

[57] ABSTRACT

The protein fraction from Leguminosae seeds, which is characterized by at least one band in polyacrylamide gel electrophoresis with sodium dodecyl sulfate, by relative molecular masses from 3,000 to 30,000 g/mole, by a content of total nitrogen of 14 to 20% and amino nitrogen of 1 to 2% related to the protein content and by further parameters defined in claim 1, is appropriate for the care of skin and for the treatment of inflammatory skin diseases, whereby the protein fraction is generally used as a concentrate of active substances or e.g. as a cream, lotion, emulsion, gel, face mask, powder or plaster.

13 Claims, No Drawings

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Modified-site
        ( B ) LOCATION: 1
        ( D ) OTHER INFORMATION: /label=Note
            / note="Residue 1 has an amide terminal methoxy succinyl group (MeOSuc)"

( i x ) FEATURE:
        ( A ) NAME/KEY: Modified-site
        ( B ) LOCATION: 4
        ( D ) OTHER INFORMATION: /label=Note
            / note="Reside 4 has a carboxy terminal para-nitroaniline group (pNA)"

( x i ) SEQUENCE DESCRIPTION: SEQ ID NO:1:

Ala  Ala  Pro  Val
    1

PROTEIN FRACTION FOR COSMETIC AND DERMATOLOGY CARE OF THE SKIN

The role of the skin, as an organ enveloping the organism, consists in sealing and mediating functions towards the environment. Various biochemical and biophysical systems help to maintain the integrity of this exposed organ: e.g. an immune system protects the skin against damage due to pathogenic microorganisms, the melanin-producing system regulates the pigmentation and protects the skin from radiation injuries, a lipid system produces lipid micelles which prevent excessive transdermal water loss and a regulated keratin synthesis provides the mechanically resistant horny layer. The cited systems base on complex processes the course of which is supported by enzymes and regulated by enzyme inhibitors. Even a slight inhibition or disinhibition of these biochemical systems leads to perceptible changes in the skin. The visible and perceptible state of the skin is, however, considered to be a measure for beauty, health and youngness; its maintenance constitutes a general purpose of skin care cosmetics.

The moisture content of the skin plays a decisive role in its appearance, elasticity and perceptible texture. An extensible, elastic limiting membrane, the stratum conjunctum, lying between the horny layer and the living epidermis, prevents healthy skin from a transdermal water loss. This permeability barrier consists of lipids, proteins and carbohydrates and may therefore be damaged by very different influences. E.g. washing with tensides can extract lipids and thereby increase the water permeability of the stratum conjunctum, ultraviolet irradiation can catalyse a reticulation or splitting of proteins, proteoglycans and polysaccharides, thereby producing a decrease in elasticity and a greater vulnerability of the stratum conjunctum, bacterial enzymes can catalyse a degradation of proteins and carbohydrates of the stratum conjunctum and, in case of inflammatory processes and immune reactions, excessively mobilized, endogenic enzymes such as tryptases, elastases and cathepsins can attack the skin and particularly its permeability barrier.

With the aim of increasing the moisture content of the skin and thereby ameliorating its state, various cosmetic skin care products have been developed. A review on hydrating cosmetic active ingredients can be found in S. D. Randazzo and P. Morganti, J. Appl. Cosmetol. 8, 93–102 (1990). Hydrophilic, hygroscopic substances such as glycerin, sorbit, various sugars or protein hydrolyzates are used. Although all these substances are removed under slight washing, some of them leave an unpleasant, sticky feeling on the skin surface and others, in the case of particularly marked hygroscopic properties, may further dry up even the horny layer. In order to provide skin with more moisture, water-in-oil emulsions are used too. However, they leave a tightly closing layer of fat, cause a water congestion, an unpleasant swelling of the horny layer and in the long term a badly repairable disturbance of the lipid composition in the stratum conjunctum. Skin care products which contain glycolipids and phospholipids from bovine brain to strengthen the permeability barrier produce a measurably higher moisture content in the skin of test persons and do not form thereby the undesired, impermeable fatty film on the horny layer. Nevertheless, since lipids from bovine brain may be potential carriers of the pathogenic agent of bovine spongiform encephalopathy (BSE), there is only a very limited demand for those products, even when they are manufactured according to processes which quite surely exclude the contamination risk.

To find out possible alternatives to active ingredients from bovine origin, the hydrating action of various plant lipids and proteins was investigated on test persons. It has been found that locally applied proteins extracted from seeds of Leguminosae particularly strongly increase the moisture content of the skin and that this effect is markedly persistent when compared to known hydrating products. It has also surprisingly been found that, in some test persons, preparations of proteins from seeds of Leguminosae soothe the itching due to insect bites and, in test persons suffering from psoriasis, they clearly reduce itching, skin redness and desquamation at the sites of lesion. Moreover, in a subsequent systematic investigation of the anti-inflammatory effect of proteins from seeds of leguminous plants, it has been found that these substances weaken the local skin redness caused on test persons by trichlorethylene quicker than an analogous preparation without proteins from Leguminosae and that the anti-inflammatory effect observed is approximately equivalent to that of a control product containing flumethasone. It has also been found that the elasticity of skin sites which were treated with proteins from seeds of Leguminosae increase in a measurable manner. Furthermore, it has been found that the cited proteins from seeds of Leguminosae inhibit proteinases such as tryptase, PMN elastase, fibroblast elastase and trypsin.

The present invention relates to a protein fraction and active concentrates containing same and to preparations for the skin care and/or treatment of inflammatory skin diseases which contain at least one protein or protein fraction obtainable from seeds of Leguminosae having an anti-inflammatory, hydrating, skin elasticity-increasing, PMN elastase and fibroblast elastase inhibiting effect.

As seeds of leguminous plants for the production of proteins of the present invention, bean species such as *Phaseolus angularis, Phaseolus lunatus, Phaseolus aureus, Phaseolus vulgaris, Phaseolus coccineus, Phaseolus limensis,* pea species such as *Lathyrus odoratus,* the soybeans *Glycine max* and *Glycine hispida,* the peanut *Arachis hypogaea* as well as the seeds of tropical leguminous plants of the genus Cajanus, Dolichus, Vigna and Vicia can be used.

The protein fractions of the present invention can be obtained from the cited seeds of leguminous plants by grinding the dried seeds, extracting the obtained flour with an organic solvent or a mixture of solvents, drying and extracting the flour defatted in such a way with water or an aqueous electrolyte solution at a pH of 2 to 10, preferably at pH 5 to 6, adjusting the extract to pH 5 to 7, concentrating under vacuum, clarifying filtering or centrifuging the concentrate under addition of a filter aid such as kieselguhr, separating the proteins therefrom either by salt precipitation, e.g. with ammonium sulfate at 30 to 80% w/v saturation, or by precipitation with an organic, watermiscible solvent such as ethanol in a concentration of 60 to 90% v/v, collecting by filtration or centrifugation and finally either drying directly in the vacuum or first removing salts by dialysis, gel filtration or ultrafiltration and then lyophilizing. A protein fraction is obtained as a dry substance which is polyacrylamide gel electrophoresis in the presence of sodium dodecyl sulfate under non-reducing conditions (Phastsystem, Pharmacia Biosystems, Uppsala, S) shows at least one band the electrophoretic mobility of which allows to deduce relative molecular masses from 3,000 to 30,000 Da, compared to a standardized protein and peptide molecular weight calibration test. The obtained protein fraction has a content of total nitrogen of 14 to 20% w/w and amine nitrogen of 1 to 2% w/w related to the protein content, is soluble in water and aqueous electrolyte solutions, is insoluble in ethanol and acetone and shows a strong precipitation in aqueous solution after addition of trichloracetic acid, sulfosalicylic acid, picric acid or benzethonium chloride. Moreover, the protein fraction inhibits proteinases and shows e.g. measured on trypsin an $I_{50}$-value of less than 10 μg/ml of test mixture, measured on PMN elastase an $I_{50}$-value of less than 100 μg/ml, measured on tryptase, an $I_{50}$-value of less than 200 mg/ml and measured on fibroblast elastase an $I_{50}$-value of less than 350 mg/ml (all related to the dry substance). The obtained protein fraction incorporated in adequate cosmetic or dermatological C vehicles in concentrations of 0.1 to 2% w/w (calculated as the dry substance) exerts a hydrating, itch-soothing, anti-inflammatory and elasticity-increasing effect on the skin of test persons.

For their dermatological and cosmetic application, the substances of the present invention are preferably incorporated in a vehicle kind to the skin, e.g. as a cream, lotion, gel, face mask, powder or plaster. In general, the finished preparations except for plasters contain 0.01 to 5 mass %, preferably 0.1 to 2 mass %, of the active principle as a dry substance. Plasters for the transdermal application of a preparation of the present invention, however, can contain up to 90 mass % of active substance. To facilitate the formulation of liquid or semi-solid preparations, stable concentrates of active substances in well-measurable doses with a content of active principle as a dry substance of 1 to 15 mass %, preferably approximately 7.5 mass %, can be manufactured from the protein fractions by dissolving the protein fractions of the present invention in water and adding a water-soluble preservative such as methyl-p-oxybenzoate to prevent microbial growth, a polyvalent alcohol such as ethylene glycol or propylene glycol for protein stabilization and a non-ionogenic or amphoteric tenside such as polysorbate 80, octoxynol, cocoamphoglycinate or cocoamidopropylbetaine to repress hydrophobic interactions and involved protein flocculation.

To determine the anti-inflammatory effect of the preparations of the present invention, e.g. the trichlorethylene erythema test according to H. Friderich (Ärztliche Forschung 20, 549–552, 1966) and for its photometric evaluation a remmission colorimeter such as the Chroma-Meter CR-300 from the firm Minolta Camera Co., Osaka, Japan can be used.

The skin elasticity can be measured by aspirating the skin of a test person with a hollow tube placed under a defined negative pressure, measuring the depth of penetration of the skin in the tube, then normalizing the pressure by ventilation and measuring again the depth of penetration of the relieved skin in the tube. The rapidity and the degree of retrogression of the skin stretched under negative pressure constitute a measure for the skin elasticity. For measuring the skin elasticity according to this principle, the recording device provided with a microprocessor "Cutometer" from the firm Courage & Khazaka Electronic GmbH, Cologne, Germany is very appropriate. The moisture degree of the skin can be measured by means of the electronic measuring device "Corneometer" (Courage & Khazaka). This principle of measure bases on the different dielectric constants of water and other components of skin.

For the in vitro determination of the elastase-inhibiting effect of the preparations of the present invention, the enzyme to be inhibited is incubated with the inhibitor or with placebo, respectively, for a determined time period, then mixed with a chromogenic proteinase substrate and the p-nitroaniline release catalyzed by the residual, non-inhibited enzyme per time unit is measured photometrically at a wave length of 405 nm as $DA_{405}/t$. The $I_{50}$-value is calculated from the difference between DA/t reference and DA/t sample as the quantity of preparation which inhibits the enzyme by 50% under the conditions defined. A chromogenic substrate adequate for PMN elastase and fibroblast elastase are MeOSuc-Ala-Ala-Pro-Val-pNA, (SEQ ID NO.: 1) (a detailed description of the methods for the determination of proteinases and their inhibitors by means of chromogenic substrates can be found in I. Witt, Eur. J. Clin. Chem Clin. Biol. 29, 355–374, 1991).

The elastase inhibiting effect may also be demonstrated in the lysate of cultured fibroblasts. The determination is performed as described above by means of a chromogenic proteinase substrate.

To show the elastase inhibition in an ex vivo system, elastin-rich tissue such as a tendon can be damaged in an organ bath by the addition of PMN elastase. This can be prevented by the simultaneous addition of the preparation of the present invention.

EXAMPLE 1

Manufacture of an Anti-Inflammatory Protein Fraction from Soybeans 100 g Of dried soybeans were ground stirred twice with each 300 ml of octane for 3 hours, filtered through a filter, thoroughly squeezed and defatted and dried under vacuum. The dried material was suspended in 1.35 l of demineralized and 0.5% w/w of the bacteriostatic agent Phenonip$^R$-containing water, the pH of the suspension was adjusted to 2.5 to 3 with hydrochloric acid, the mixture was stirred for 2 hours at 20° C. and then centrifuged. The opalescent supernate was adjusted to pH 5.2, concentrated to 200 ml under vacuum at 40° to 50° C., mixed with 400 ml of saturated ammonium sulfate solution and let stand for 15 hours at room temperature. The protein precipitations were separated by centrifugation, suspended in 100 ml of aqueous Phenonip$^R$ solution 0.5% w/w, dialyzed overnight against 2 l of Phenonip$^R$ water, freed from the precipitated material by filtration through an asbestos-free filter bed and then lyophilized. A protein fraction was obtained which in polyacrylamide gel electrophoresis in the presence of sodium dodecyl sulfate under non-reducing conditions showed 4 bands the electrophoretic mobility of which allowed to deduce relative molecular masses from 3,000 to 30,000 Da. The obtained protein fraction had a content of total nitrogen of 15.2% w/w and amino nitrogen of 1.4% w/w elated to the protein content, was soluble in water and aqueous electrolyte solutions, was insoluble in ethanol and acetone, showed a strong precipitation in aqueous solution after addition of trichloracetic acid, sulfosalicylic acid, picric acid or benzethonium chloride and measured on trypsin presented an $I_{50}$-value of 3 μg (related to the dry substance) per ml of test mixture and, measured on PMN elastase, an $I_{50}$-value of 68 μg (related to the dry substance) per ml. The obtained protein fraction, incorporated in a cosmetic lotion in a concentration of 0.75% w/w applied on the skin of test persons, exerted a hydrating, itch-soothing, anti-inflammatory and elasticity-increasing effect.

EXAMPLE 2

Manufacture of an Anti-Inflammatory Protein Fraction from Lima Beans 100 g of dried lima beans (*Phaseolus lunatus*) were ground, stirred for 1 hour with 500 ml of ethanol 95 vol. % and filtered, the moist residue was stirred twice with each 500 ml of acetic acid 1N for 1 hour and filtered again. The pooled acetic acid extracts were concentrated to 100 ml in the vacuum, mixed with 50 vol. % ethanol, precipitated polysaccharides were removed by filtration, the active proteins were precipitated from the filtrate by increasing the ethanol concentration to 80%, collected on a filter and dried in the vacuum. A protein fraction was obtained which, in polyacrylamide gel electrophoresis in the presence of sodium dodecyl sulfate under non-reducing conditions, showed 5 bands the electrophoretic mobility of which allowed to deduce relative molecular masses from 3,000 to 30,000 Da. The obtained protein fraction had a content of total nitrogen of 14.9% w/w and amino nitrogen of 1.3% w/w related to the protein content, was soluble in water and aqueous electrolyte solutions, was insoluble in ethanol and acetone, showed a strong precipitation in aqueous solution after addition of trichloracetic acid, sulfosalicylic acid or picric acid and, measured on trypsin, presented an $I_{50}$-value of 5 μg (related to the dry substance) per ml of test mixture and, measured on PMN elastase, an $I_{50}$-value of 89 μg (related to the dry substance) per ml. The obtained protein fraction, incorporated in a cosmetic lotion in a concentration of 1.5% w/w, applied on the skin of test persons, exerted a hydrating, itch-soothing, anti-inflammatory and elasticity-increasing effect.

EXAMPLE 3

Manufacture of a Stable Concentrate of Active Substances 20 g of propylene glycol, 2 g of Tween 80 and 0.2 g of methyl-p-oxybenzoate were dissolved in 60 ml of distilled water under heating to 70° C. After cooling to 30° C., 7.5 g of the protein fraction manufactured according to example 1 were dissolved in this solution, the pH was adjusted to 7 and the volume completed to 100 ml with distilled water.

EXAMPLE 4

Determination of the Anti-Inflammatory Effect of a Soya Protein Fraction

Nine volume parts of the commercially available, skin-compatible, active ingredient-free emulsion "Excipial U Lotio" (Spirig AG, Egerkingen, Switzerland) were mixed with one volume part of distilled water (placebo) or of the sample manufactured according to example 1, pre-diluted in distilled water in a concentration of 75 mg per ml, respectively, and homogenized. The skin of the forearm of 2 volunteers was irritated on 4 places each with a patch test plaster impregnated with 150 μl of trichlorethylene for 5 minutes. Afterwards, each 2 of the irritated skin areas were treated with the placebo emulsion or with the sample, respectively. The intensity of the skin redness was measured by means of the chromameter every 5 minutes for a total of 90 minutes. The progression of the measured and averaged extinction values is shown in Table 1 and demonstrates a considerably weaker intensity of redness for the sample than for the placebo, redness which decreases also more rapidly to the norm again.

TABLE 1

| Time (min.) | Extinction placebo | Extinction sample | Difference |
|---|---|---|---|
| 5 | 7.20 | 6.90 | 0.30 |
| 10 | 6.98 | 6.82 | 0.16 |
| 15 | 7.04 | 6.93 | 0.11 |
| 20 | 7.06 | 6.47 | 0.59 |
| 25 | 6.55 | 5.71 | 0.84 |
| 30 | 6.03 | 5.39 | 0.64 |
| 35 | 4.91 | 4.56 | 0.35 |
| 40 | 4.58 | 3.99 | 0.56 |
| 45 | 3.65 | 3.10 | 0.55 |
| 50 | 3.82 | 2.47 | 0.81 |
| 55 | 2.85 | 2.22 | 0.63 |
| 60 | 2.38 | 1.83 | 0.55 |
| 65 | 1.96 | 1.40 | 0.56 |
| 70 | 2.15 | 1.29 | 0.86 |
| 75 | 1.74 | 1.00 | 0.74 |
| 80 | 1.25 | 0.93 | 0.32 |
| 90 | 1.29 | 1.29 | 0 |

EXAMPLE 5

Determination of the Elastase-Inhibiting Activity of a Lima Bean Protein Fraction 500 μl of a solution of MeOSuc-Ala-Ala-Pro--Val-pNA, (SEQ ID NO.: 1) 1 mM, in albumin-containing buffer pH 7.5, were mixed with 10 μl of samples from an aqueous dilution series of the protein fraction manufactured according to example 2 or with 10 μl of distilled water (reference), respectively, and pre-incubated at 37° C. for 15 minutes. To each test preparation, 100 μl of PMN elastase, 100 nM, were added, the p-nitroaniline release was registered for 10 minutes at 405 run by means of a recording photometer, the absorption differences per minute (DA/min) were calculated therefrom and then the elastase inhibition was calculated in % according to the following equation:

$$\% \text{ inhibition} = \frac{DA_{ref}/\text{min} - DA_{sample}/\text{min}}{DA_{ref}/\text{min}} \times 100$$

From a dose-effect graph, an $I_{50}$-value (PMN elastase) of 89 mg/l (related to the dry substance) was determined for the protein fraction.

EXAMPLE 6

Determination of the Trypsin-Inhibiting Activity of an Anti-Inflammatory Protein Fraction from Soybeans 0.100 ml of trypsin solution, 30 U/ml, were mixed with 0.100 ml of samples from an aqueous dilution series of the protein fraction manufactured according to example 1 or with 0.100 ml of distilled water (reference), respectively, and kept at room temperature for one minute. To each test preparation, 1.7 ml of Tris-imidazole buffer pH 8.4 and 0.100 ml of a 4 millimolar solution of Bz-Val-Gly--Arg-pNA were added at 37° C. and the p-nitroaniline release was registered for 10 minutes by means of a recording photometer, the absorption differences per minute (DA/min) were calculated therefrom and then the trypsin inhibition was calculated in % according to the following equation:

$$\% \text{ inhibition} = \frac{DA_{ref.}/\text{min} - DA_{sample}/\text{min}}{DA_{ref.}/\text{min}} \times 100$$

From a dose-effect graph, an $I_{50}$-value of 3 mg/l (related to the dry substance) was determined for the protein fraction.

EXAMPLE 7

Determination of the Tryptase-Inhibiting Activity of an Anti-Inflammatory Protein Fraction from Soybeans 125 µl of heparin diluted in buffer (c=10 mg/ml) as well as 125 µl of Tos-Gly-Pro-Arg-pNA 1.5 mM were pipetted into 1000 µl of Tris-HCl buffer, pH 7.6, containing varying volume parts of the stable concentrate of active substances manufactured according to example 3. 125 µl of human tryptase from lung (c=28 U/ml) were added to each test preparation and the p-nitroaniline release was registered at 25° C. with a recording photometer for 3 minutes at 405 nm, the absorption differences per minute (DA/min) were calculated therefrom and then the tryptase inhibition was calculated in % according to the following equation:

$$\% \text{ inhibition} = \frac{DA_{ref.}/\text{min} - DA_{sample}/\text{min}}{DA_{ref.}/\text{min}} \times 100$$

From a dose-effect graph, an $I_{50}$-value of 160 mg/ml was determined for the active substance concentrate.

EXAMPLE 8

Effect of an Anti-Inflammatory Protein Fraction in an Ex Vivo Test System

A tendon, isolated from the tail of a white mouse of the strain NMRI, was fixed at room temperature in an organ bath containing 0.5 ml of tyrode solution pH 7.4. The tendon was attached by means of a thread to a lever arm which converted any change in the length of the tendon into an electronic signal which was amplified and registered with a potentiometric recorder. After 20 minutes of pre-incubation, the tyrode solution was replaced by an adequate volume of tyrode solution containing on one hand 38 µg of PMN elastase (=reference solution) and on the other hand 38 µg of PMN elastase and 100 µl/ml of the active substance solution manufactured according to example 3 (=test solution). In the case of the reference solution, a continuous stretching of the tendon could be registered, which finally tore after 132 minutes. No change in the tendon length was observed in the case of the test solution.

EXAMPLE 9

Determination of the Elastase-Inhibiting Effect of an Anti-Inflammatory Protein Fraction in Fibroblast Cultures Swiss 3T3 mouse fibroblasts with a density of $10^8$ cells per 175 cm$^2$ were lysed with 10 ml of 50 mM Tris/HCl pH 8.0 containing 1% Triton X-100 for 30 minutes at 4° C. The cell fragments were separated by centrifugation for 15 minutes at 5000 g and 0° C. 500 µl of lysate were mixed with 500 µl of various concentrations of the active substance concentrate manufactured according to example 3 and 34 µl of a solution of MeO-Suc-Ala-Ala-Pro-Val-pNA and the p-nitroaniline release was registered with a recording photometer for 2 hours at 405 nm, the absorption differences per minute (DA/min) were calculated therefrom and then the elastase inhibition was calculated in % according to the following equation:

$$\% \text{ inhibition} = \frac{DA_{ref.}/\text{min} - DA_{sample}/\text{min}}{DA_{ref.}/\text{min}} \times 100$$

From a dose-effect graph, an $I_{50}$-value (fibroblast elastase) of 280 mg/ml was determined for the active substance concentrate.

EXAMPLE 10

Manufacture of a Cosmetic Cream (Oil-in-Water Emulsion)

| | |
|---|---|
| Active substance concentrate according to example 3 | 10.0 g |
| Polysorbate 60 | 3.0 g |
| Sorbitan stearate | 2.0 g |
| Cetyl alcohol | 3.0 g |
| Stearic acid | 6.0 g |
| Isopropyl myristate | 10.0 g |
| Capryl-capric acid-triglycerides | 5.0 g |
| Phenonip ® | 0.5 g |
| Demineralized water | 56.2 g |
| Propylene glycol | 4.0 g |
| Imidazolinidyl urea | 0.3 g |

All the components except for the active substance concentrate are mixed at 70° C. under strong stirring, allowed to cool down and then mixed with the active substance concentrate.

EXAMPLE 11

Manufacture of a Lotion for the Treatment of Inflammatory Skin Diseases

| | |
|---|---|
| Active substance concentrate according to example 3 | 5.0 g |
| Stearyl alcohol | 1.0 g |
| Cetearate 6 | 1.0 g |
| Cetearyl alcohol | 7.0 g |
| Mineral oil | 8.0 g |
| Cetyl alcohol | 1.0 g |
| Glyceryl stearate | 2.5 g |
| Phenonip ® | 0.3 g |
| Demineralized water | 72.0 g |
| Propylene glycol | 2.0 g |
| Imidazolinidyl urea | 0.2 g |

All the components except for the active substance concentrate are mixed at 70° C. under strong stirring, allowed to cool down and then mixed with the active substance concentrate.

EXAMPLE 12

Manufacture of a Skin Care Gel

| | |
|---|---|
| Active substance concentrate according to example 3 | 5.0 g |
| Demineralized water | 88.5 g |
| Phenonip ® | 0.3 g |
| Imidazolinidyl urea | 0.2 g |
| Propylene glycol | 5.0 g |
| Cellulose rubber | 1.0 g |

All the components are dissolved under stirring in demineralized water at 40° C.

EXAMPLE 13

Effect of a Soya Protein Fraction on the Moisture Content of the Skin

During a test period of 7 days, 60 μl of active substance concentrate manufactured according to example 3 were distributed on 20 cm² of the inner side of the left forearm of 5 test persons on 5 days; the untreated right arm served as the control. Two hours after the application, the skin moisture expressed in corneo-units (CU) was measured and the increase in the moisture content of the skin was calculated in % from the measured values in comparison with the initial value. The results are represented in Table 2 as means of 5 test persons.

TABLE 2

| Day | Corneo-Units Sample | Corneo-Units Control | Increase (%) Sample | Increase (%) Control |
|---|---|---|---|---|
| 1 | 61.4 | 59.33 | 0 | 0 |
| 3 | 82.4 | 63.6 | 34.2 | 7.2 |
| 4 | 88.8 | 67 | 44.6 | 12.9 |
| 5 | 89.2 | 64.8 | 45.3 | 9.2 |
| 6 | 88 | 60.2 | 43.3 | 1.5 |
| 7 | 85 | 62.4 | 38.4 | 5.2 |

EXAMPLE 14

Effect of a Soya Protein Fraction on the Elasticity of the Skin

60 μl of the active substance concentrate manufactured according to example 3 were applied twice a day on the corner of the left eye of 5 test persons; the untreated right corner of the eye served as the control. Before beginning as well as 14 days after the treatment, the elasticity of the skin was determined by measuring the depth of penetration of the skin in a hollow tube placed under negative pressure as well as the retrogression of the skin under normal pressure. The difference in the depths of penetration of the skin placed 5 successive times under pressure and then relieved again (=ds) is a measure for the skin elasticity. The smaller the difference, the greater the elasticity. The results are represented in Table 3 as means of 5 test persons.

TABLE 3

|  | ds left (sample) | ds right (control) |
|---|---|---|
| before treatment | 0.067 mm | 0.057 mm |
| after treatment | 0.042 mm | 0.058 mm |

---

---

We claim:

1. Protein fraction which contains at least one protein which comprises
  a) its isolation from leguminosae seeds,
  b) at least one band in polyacrylamide gel electrophoresis with sodium dodecyl sulfate under non-reducing conditions,
  c) molecular weights from about 3,000 to 30,000 Da,
  d) a content of total nitrogen of about 14% to 20% w/w and amino nitrogen of about 1% to 2% w/w related to the protein content,
  e) its solubility in water and aqueous electrolyte solutions and its insolubility in ethanol and acetone,
  f) its precipitation in aqueous solution after addition of trichloracetic acid, sulfosalicylic acid, picric acid or benzethonium chloride, and
  g) its inhibition of PMN elastase and fibroblast elastase.

2. Protein fraction according to claim 1 wherein the Leguminosae seeds are soya or lima beans.

3. Stable aqueous concentrate of active substances which contains 1 to 15 weight % related to the weight of the active concentrate of a protein fraction according to claim 1 and at least one water-soluble preservative, at least one polyvalent alcohol and a non-inorganic or amphoteric tenside.

4. Concentrate of active substances according to claim 2 which contains methyl-p-oxybenzoate as the water-soluble preservative, propylene glycol as the polyvalent alcohol and polysorbate 80, octoxynol, or cocoamphoglycinate as the tenside.

5. The concentrate according to claim 3 wherein the protein fraction is present in an amount of about 7.5 weight %.

6. Preparations for the care of skin and/or treatment of inflammatory diseases thereof comprising a carrier and the protein fraction according to claim 1 in an amount of about 0.01 to 5 weight % based upon the total weight of the preparation.

7. Preparations applied on a plaster for transdermal application wherein the preparation contains a protein fraction according to claim 1 in a quantity of up to 90 weight % based on the total weight of the preparation.

8. Preparations for the care of skin and/or treatment of inflammatory diseases thereof comprising a carrier and the concentrate according to claim 3 in an amount of about 0.01 to 5 weight % based upon the total weight of the preparation.

9. The preparation according to claim 6 in which the protein fraction is present in an amount of about 0.1 to 2 weight %.

10. Process for treating the skin or inflammatory diseases thereof which comprises administering to skin in need of such treatment the concentrate according to claim 3 in an amount which is therapeutically effective for treatment thereof.

11. Process for treating the skin or inflammatory diseases thereof which comprises administering to skin in need of such treatment the preparation according to claim 6 for treatment thereof.

12. A process for treating the skin or inflammatory diseases thereof which comprises administering to skin in need of such treatment the protein fraction according to claim 1 in an amount which is therapeutically effective for treatment thereof.

13. A process for treating the skin or inflammatory diseases thereof which comprises administering to skin in need of such treatment the concentrate according to claim 4 in an amount which is therapeutically effective for treatment thereof.

* * * * *

UNITED STATES PATENT AND TRADEMARK OFFICE
CERTIFICATE OF CORRECTION

PATENT NO. : 5,322,839

DATED : June 21, 1994

INVENTOR(S) : Rainer Voegeli et al.

It is certified that error appears in the above-identified patent and that said Letters Patent is hereby corrected as shown below:

Column 11:
    Claim 4 should depend upon claim 3.

Signed and Sealed this

Third Day of January, 1995

Attest:

BRUCE LEHMAN

*Attesting Officer*      *Commissioner of Patents and Trademarks*